United States Patent [19]

Lacoste

[11] Patent Number: 4,481,686
[45] Date of Patent: Nov. 13, 1984

[54] AIR FLUIDIZED BED FOR THERAPEUTIC USE

[76] Inventor: Francois R. Lacoste, 35 Boulevard d'Inkermann, 92200 Neuilly, France

[21] Appl. No.: 477,497

[22] Filed: Mar. 21, 1983

[30] Foreign Application Priority Data

Mar. 25, 1982 [FR] France .................. 82 05064

[51] Int. Cl.³ .............................................. A61G 7/04
[52] U.S. Cl. ........................................... 5/453; 5/423; 128/38
[58] Field of Search .................. 5/453, 454, 450, 461, 5/469, 423, 438; 128/38

[56] References Cited

U.S. PATENT DOCUMENTS 3,428,973 2/1969 Hargest et al. .................... 5/423
3,459,179 8/1969 Olesen ................................. 5/481
3,968,530 7/1976 Dyson .................................. 5/436
4,139,920 2/1979 Evans ................................. 5/455

Primary Examiner—Alexander Grosz
Attorney, Agent, or Firm—Marshall, O'Toole, Gerstein, Murray & Bicknell

[57] ABSTRACT

An air-fluidized bed for therapeutic use of the type comprising a tank filled with a particulate material through which passes an upward flow of gas.

According to the invention, particles of spherical shape, with a density higher than that of the particulate material, and which have a greater biochemical activity than the particulate material, are introduced in the tank.

Application: control of the bactericidal activity of an air-fluidized bed.

4 Claims, 2 Drawing Figures

AIR FLUIDIZED BED FOR THERAPEUTIC USE

The present invention relates to an air-fluidized bed for therapeutic use intended, particularly but not exclusively, for the treatment of patients with burns or decubitus ulcers.

Beds of this type are well-known and their use in hospitals is spreading quickly. They are described for example in U.S. Pat. No. 3,428,973 dated Mar. 17, 1966. Each bed comprises a tank filled with a particulate material and a device for blowing a compressed gas through the particulate material so that it becomes fluidized without being expelled from the tank. The lower part of the tank is made of a diffusion screen sufficiently porous to allow the gas in the tank without allowing the particulate material out of the tank.

In actual practice, the particulate material is made of small glass spheres with a diameter of approximately 3 thousandths of an inch and the average density of the material after fluidization is between 1.6 and 1.7 The patient is therefore supported on the bed as if he was floating on a liquid of high density. The result is a uniform pressure on all the supporting surface of the patient and therefore a feeling of great comfort. To prevent the direct contact of the small spheres with the skin of the patient, a porous sheet is applied on the surface of the particulate material, thus allowing the gas out (in actual practice air) while retaining the small spheres.

Owing to the risks of contamination of the open wounds of the patients treated on these beds, systematic studies of their microbiological environment have been undertaken. These studies have shown that the beds have bacteristatic and even, in most cases, bactericidal properties towards most bacterial species encountered. Explanation of this favourable phenomenon seems to be, on the one hand the dessication effect of the fluidizing air and, on the other hand the moderately basic characteristic of the material due to the sodium ions present on the surface of the glass of which the small spheres are made. Some part seems also to be played by the glass dust produced by the erosion of the small spheres.

However, these favourable characteristics are offset on the one hand by a fine layer of antifriction material covering the spheres to facilitate their fluidization, which cuts out essentially contact between the glass material and the external medium and, on the other hand by the variable proportion of glass dust existing in the material, depending on the production lots, this proportion being also capable of variation with the level of erosion of the spheres and the filtration capability of the sheet covering them. Furthermore, the use of a material other than glass could put in question the moderately basic characteristic of the present medium. Finally, the necessity of treating patients carrying specially resisting microbial species could appear in the future. It appears therefore desirable to control the biochemical behaviour of the particulate material.

The present invention is based on the idea that it is possible to use the inert particulate material supporting the patient as a therapeutic bactericidal agent.

According to the present invention, the air-fluidized bed comprising a tank filled with a particulate material through which passes a vertical upward flow of gas, the material being covered by a porous sheet, is characterized by the introduction in said particulate material of bactericidal particles having a greater activity than said particulate material, said particles representing only a small fraction of the whole material.

It is therefore possible to control the biochemical action of the material by introducing in it a variable proportion of particles more or less active.

According to another feature of the invention, said particles are preferably spherical. This shape contributes to a good fluidization, the spherical shaped particles being capable of moving more easily among the small glass spheres.

Other characteristics and advantages of the invention will become more clearly apparent in the light of the description which is to follow, given by way of illustration but in no way restrictively, by reference to the Figures of the attached drawing in which.

Figure 1:
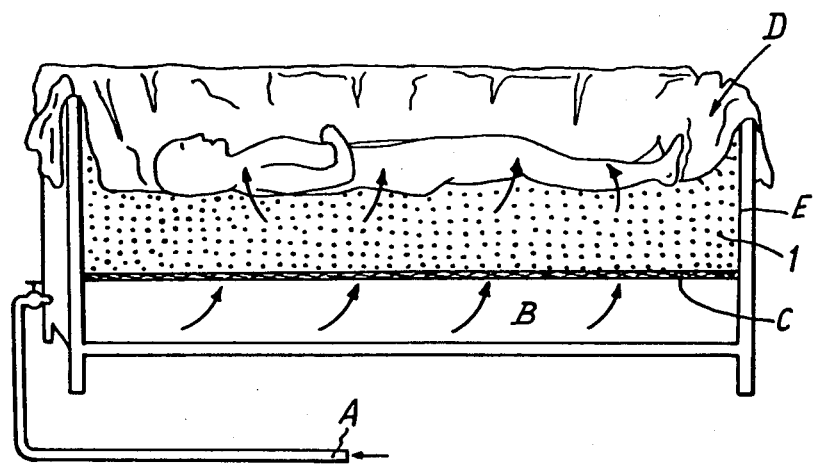
FIG. 1 is an air-fluidized bed of a known type.

In FIG. 1, the air-fluidized bed comprises a tank E containing a particulate material, made of glass or ceramic spheres 1 for instance. The lower part of the tank E is made of a diffusing porous screen C on top of a compression chamber B supplied with gas by a nozzle A. The top surface of the particulate material is covered by a porous sheet D on which the patient is lying. The arrows indicate roughly the direction of flow of the fluidizing air, or gas. In practice, the small spheres 1, under the influence of the gas and their mutual contacts, have motions of the brownian type.

As stated hereabove, the invention relates to a method for controlling the bactericidal activity of the particulate material by the introduction in said material of particles which are preferably spherical so as to facilitate, on the one hand the flow of the gas and, on the other hand the intimate mixing of the glass spheres and the bactericidal particles. Preferably, the size of the particles is similar to the size of the glass spheres so that their specific active surface per unit of weight is as high as possible.

According to another feature of the invention, the density of the material of which the particles are made is slightly higher than the density of the material of which the inert spheres are made. Thus, the particles, which could have an adverse action, are not in direct contact with the sheet supporting the patient.

Figure 2:
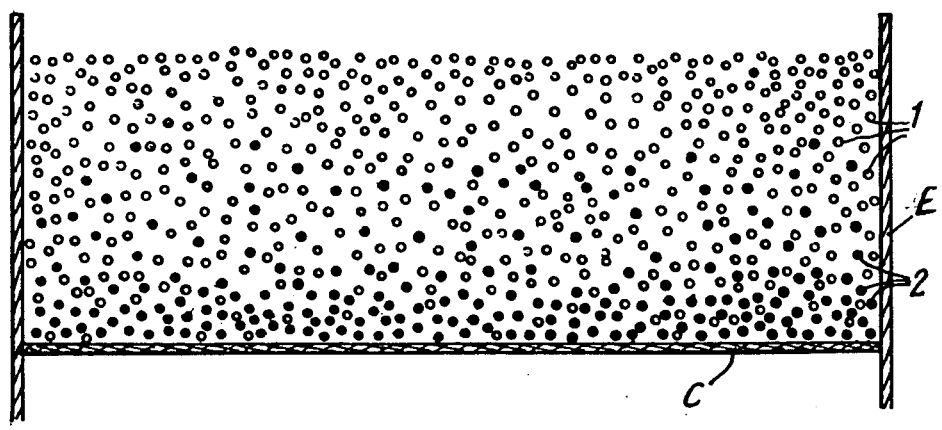
FIG. 2 is an example of the distribution of the bactericid particles in the particulate material.

FIG. 2 shows a schematic distribution of the particles 2 inside the small spheres 1. Under the influence of the motion produced by the flow of the gas and of the different densities of the two components of the mixture, a statistical equilibrium establishes itself in such a manner that the proportion of the particles mixed with the small spheres increases downwards. Naturally, this equilibrium establishes itself only when the flow of gas is continuous. Thus, the particles assemble in the lower part of the tank and all contact with the patient's wounds is prevented. Also, the biochemical activity of the material of which the particles are made, although higher than the activity of the glass spheres, should be somewhat limited so that the dust, produced by the wear of the particles and which could go through the porous sheet, should not inflame the wounds.

A systematic search of the materials which could be used to make particles satisfying the hereabove contraints has lead to the alkaline earth metals such as calcium and magnesium, to the alloys of these two metals together and with other elements of higher density and lower activity such as aluminum bismuth and silicon. Calcium and magnesium reacts spontaneously when in contact with air and the oxides thus produced react with water to give a basic compound quite active, specially in the case of calcium but also in the case of magnesium. By alloying these two elements with the less active elements given hereabove, one can obtain the level of biochemical activity desired.

The fluids coming from the patient, which are generally acid, flow downwards by gravity through the small spheres which they agglomerate temporarily. At some time, during their transfer, they come in contact with the particles and react with them to give a salt by-product while the microbial species are destroyed.

It goes without saying that the invention cannot be restricted to the examples of it which have been given by way of illustration but comprises any variant which takes up with equivalent means the general definition appearing in the claims.

I claim:

1. An air-fluidized bed for therapeutic use comprising a tank filled with a particulate material through which air flows upwardly, the material being covered by a porous sheet, characterized by the introduction, in said particulate material, of spherical particles having a size of the same order of magnitude as said particulate material and greater biochemical activity than said particulate material, said particles having a density higher than that of said particulate material.

2. An air-fluidized bed according to claim 1, characterized by the fact that said particles are made of at least one element selected from the class consisting of calcium, magnesium, aluminum, bismuth and silicon.

3. An air-fluidized bed for therapeutic use comprising a tank filled with a particulate material through which air flows upwardly, the material being covered by a porous sheet, characterized by the introduction, in said particulate material, of particles having greater biochemical activity than said particulate material, said particles having a density higher than that of said particulate material.

4. An air-fluidized bed according to claim 3, characterized by the fact that said particles are made of at least one element selected from the class consisting of calcium, magnesium, aluminum, bismuth and silicon.

* * * * *